United States Patent [19]

Drabek

[11] Patent Number: 4,786,650
[45] Date of Patent: Nov. 22, 1988

[54] 3-ACYLAMINOBENZISOTHIAZOLE-S,S-DIOXIDE AND INSECTICIDAL COMPOSITIONS AND METHODS

[75] Inventor: Josef Drabek, Oberwil, Switzerland

[73] Assignee: Ciba-Geigy Corporation, Ardsley, N.Y.

[21] Appl. No.: 825,304

[22] Filed: Feb. 3, 1986

[30] Foreign Application Priority Data

Feb. 13, 1985 [CH] Switzerland .......................... 649/85

[51] Int. Cl.[4] .................... A01N 43/80; C07D 275/06
[52] U.S. Cl. ..................................... 514/373; 548/209
[58] Field of Search ............... 548/209, 206, 207, 212; 514/373

[56] References Cited

U.S. PATENT DOCUMENTS 4,379,157 4/1983 Van Hess et al. .................. 548/207

FOREIGN PATENT DOCUMENTS 0110829 6/1984 European Pat. Off. ............ 548/212
0133418 8/1984 European Pat. Off. .

OTHER PUBLICATIONS

Fluek, Victor; Declaration for Patent 551,766; Filed Nov. 14, 1983, Table II.

Primary Examiner—Donald G. Daus
Assistant Examiner—Diana G. Rivers
Attorney, Agent, or Firm—Kevin T. Mansfield; Edward McC. Roberts

[57] ABSTRACT

The invention relates to a novel 3-acylaminobenzisothiazole-S,S-dioxide of formula I

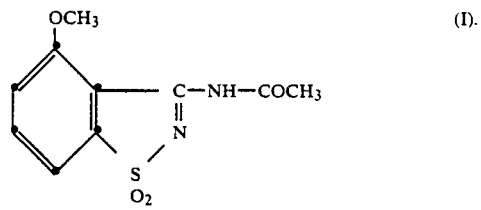

to the preparation thereof, to insecticidal compositions containing said compound and to the use thereof for controlling insects, in particular plant-destructive sucking insects.

6 Claims, No Drawings

3-ACYLAMINOBENZISOTHIAZOLE-S,S-DIOXIDE AND INSECTICIDAL COMPOSITIONS AND METHODS

The present invention relates to a novel 3-acylaminobenzisothiazole-S,S-dioxide which is suitable for controlling insects, to the preparation thereof, and to insecticidal compositions which contain said compound as active component.

The novel 3-acetylamino-4-methoxybenzisothiazole-S,S-dioxide of this invention is characterised by the formula

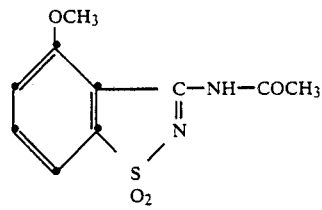

Within the scope of the present invention, the compound of formula I may also be in its tautomeric form of formula Ia

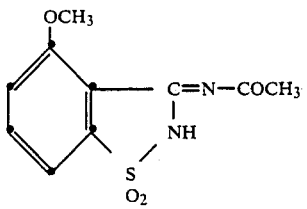

Substituted 3-aminobenzisothiazole-S,S-dioxides having aphicidal activity are already known from European patent application No. 0033984. Further, 3-acylaminobenzisothiazole-S,S-dioxides and the use thereof as insecticides are disclosed in published European patent application No. 0110829. Although the compound of formula I of this invention falls within the general scope of this prior art, it is not specifically disclosed therein. Surprisingly, it has been found that the compound of formula I is superior to the structurally similar compounds known from the aforementioned European patent application with respect to its insecticidal, in particular aphicidal, activity (q.v. Example 4 of the instant application). It was unexpected that the compound of the formula I, which can be obtained from relatively easily accessible starting materials, is suitable for the complete extermination of populations of harmful sucking insects, even when applied at low rates of application. It must also must also be mentioned that the novel compound of formula I has low toxicity to warm-blooded animals, is well tolerated by plants, has an advantageous long-term activity and can be readily formulated.

The compound of formula I of this invention can be prepared by methods analogous to known ones (q.v. for example J. March, Advanced Organic Chemistry, McGraw Hill, New York, 1977, pp. 383-385) by (a) reacting the 3-amino-4-methoxybenzisothiazole-S,S-dioxide of formula II

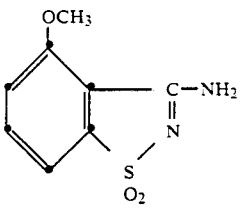

with an acetyl halide of formula III

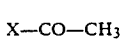

or with acetic anhydride, in the absence or presence of a base, where X in formula III is halogen, preferably chlorine; or (b) oxidising the 3-acetylamino-4-methoxybenziso-thiazole of formula IV

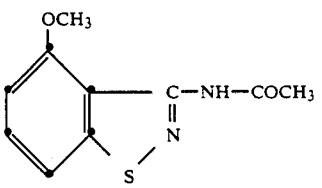

in a manner known per se.

Suitable bases for process (a) are in particular tertiary amines such as trialkylamines, dialkylanilines and p-dialkylaminopyridines. The process is generally carried out under normal pressure in the temperature range from $-25°$ to $+150°$ C., preferably from 50° to 100° C., and with or without a solvent or diluent.

Suitable oxidising agents for process (b) are peracids, e.g. performic acid, peracetic acid, substituted perbenzoic acids, sodium periodate, monopermaleic acid, monoperphthalic acid, tert-butylperbenzoic acid, trifluoroperacetic acid or hydrogen peroxide, with perbenzoic acid being preferred. The oxidation is in general carried out at a reaction temperature in the range from $-30°$ to $+120°$ C., preferably from 0° to 50° C., under normal or elevated temperature, and preferably in an inert solvent or diluent.

Suitable solvents or diluents for the process of the invention are e.g. ethers and ethereal compounds such as diethyl ether, dipropyl ether, dioxane, dimethoxyethane and tetrahydrofuran; amides such as N,N-dialkylated carboxamides; aliphatic, aromatic or halogenated hydrocarbons, preferably benzene, toluene, xylenes, chloroform and chlorobenzene; nitriles such as acetonitrile; dimethylsulfoxide and ketones such as acetone and methyl ethyl ketone; and esters such as ethyl acetate.

The starting material of formula II is known and can be prepared by methods which are known per se. Thus the preparation of 3-aminobenzisothiazole-S,S-dioxides is described in European patent application No. 0033984. The starting compound of formula IV is also known and can be obtained by acetylating 3-amino-4-methoxybenzisothiazole.

The compound of formula I is suitable for controlling insects which are pests of animals and plants.

In particular, the compound of the formula I is suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera.

Most particularly, the compound of formula I is suitable for controlling plant-destructive insects, especially plant-destructive insects in ornamentals and crops of useful plants, especially in cotton, vegetable, rice and fruit crops. In this connection, particular attention is drawn to the fact that the compound of formula I has a strongly pronounced systemic as well as contact action against sucking insects, especially against sucking insects of the family Aphididae (e.g. against *Aphis fabae, Aphis craccivora* and *Myzus persicae*) which can only be controlled with difficulty using known pesticides. The compound of formula I also has a useful action against feeding and biting insects as well as against flies, e.g. *Musca domestica*, and mosquito larvae.

The activity of the compound of formula I and of the compositions containing it can be substantially broadened and adapted to prevailing circumstances by addition of other insecticides and/or acaricides. Examples of suitable additives include: organophosphorus compounds, nitrophenols and derivatives thereof, formamidines, ureas, carbamates, chlorinated hydrocarbons, pyrethroids, and Bacillus thuringiensis preparations.

The compound of formula I can also combined with particular advantage with substances which exert a pesticidally potentiating action. Examples of such compounds comprise: piperonyl butoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioate.

The good insecticidal activity of the proposed compound of formula I according to the invention corresponds to a mortality of at least 50–60% of the above harmful insects.

The compound of formula I is used in unmodified form, or preferably together with the adjuvants conventionally employed in the art of formulation, and is therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions or preparations containing the compound (active ingredient) of formula I and, where appropriate, a solid or liquid adjuvant, are prepared in known manner, e.g. by homogeneously mixing and/or grinding the active ingredient with extenders, e.g. solvents, solid carriers, and in some cases surface-active compounds (surfactants).

Suitable solvents are: amatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated absorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures or surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixture which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonyl-phenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, adducts of polypropylene and polyethylene oxide, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or lower hydroxyalkyl radicals. The salts are preferably in the form of halides, methylsulfates or ethylsulfates, e.g. stearyltrimethylammoniumchloride or benzyldi-(2-chloroethyl)ethylammonium bromide.

The surfactants customarily employed in the art of formulation are described e.g. in "McCutcheon's Detergents and emulsifiers Annual", MC Publishing Corp. Ridgewood, N.J., 1979; Dr. Helmut Stache, "Tensid-Taschenbuch" (Handbook of Surfactants), Carl Hanser Verlag, Munich/Vienna, 1981.

The pesticidal compositions usually contain 0.1 to 99%, preferably 0.1 to 95%, of the compound of formula I, 1 to 99.9% of a solid or liquid adjuvant, and 0 to 25%, preferably 0.1 to 25%, of a surfactant.

Whereas commercial products are preferably formulated as concentrates, the end user will normally employ dilute formulations of lower concentration.

The compositions may also contain further ingredients, such as stabilisers, antifoams, viscosity regulators, binders, tackifiers as well as fertilisers or other active ingredients for obtaining special effects.

EXAMPLE 1

Preparation of 3-acetylamino-4-methoxybenzisothioazole S,S-dioxide 6.66 g of 3-acetylamino-4-methoxybenzisothiazole are mixed with 150 ml of chloroform. With stirring, 10.35 g of m-chloroperbenzoic acid are added to this mixture in portions at 20°–30° C. The reaction mixture is then stirred overnight at room temperature, filtered with suction, and the solvent is distilled off from the filtrate. The residual crude product is chromatographed through a column of silica gel (eluted with methylene chloride/isopropanol), affording colourless crystals of the title compound with a melting point of 242°–245° C.

EXAMPLE 2

Formulations for the compound of formula I according to Example 1 or combinations thereof with other insecticides (throughout, percentages are by weight)

| 2.1 Wettable powders | (a) | (b) | (c) |
|---|---|---|---|
| compound of formula I or combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient or combination is thoroughly mixed with the adjuvants and the mixture is thoroughly ground in a suitable mill, affording wettable powders which can be diluted with water to give suspensions of the desired concentration.

| 2.2 Emulsifiable concentrate | |
|---|---|
| compound of formula I or combination | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 2.3 Dusts | (a) | (b) |
|---|---|---|
| compound of formula I or combination | 5% | 8% |
| talcum | 95% | — |
| kaolin | — | 92% |

Ready for use dusts are obtained by mixing the active ingredient with the carriers, and grinding the mixture in a suitable mill.

| 2.4 Extruder granulate | |
|---|---|
| compound of formula I or combination | 10% |
| sodium lignosulfonate | 2% |
| carboxymethylcellulose | 1% |
| kaolin | 87% |

The active ingredient or combination is mixed and ground with the adjuvants, and the mixture is subsequently moistened with water. The mixture is extruded and then dried in a stream of air.

| 2.5 Coated granulate | |
|---|---|
| compound of formula I or combination | 3% |
| polyethylene glycol 200 | 3% |
| kaolin | 94% |

The finely ground active ingredient or combination is uniformly applied, in a mixer, to the kaolin moistened with polyethylene glycol. Non-dusty coated granulates are obtained in this manner.

| 2.6 Suspension concentrate | |
|---|---|
| compound of formula I or combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |

The finely ground active ingredient or combination is intimately mixed with the adjuvants, giving a suspension concentrate from which suspensions of any desired concentration can be obtained by dilution with water.

EXAMPLE 3

Insecticidal contact action against Aphis craccivora

Before the start of the test, bean plants (Vicia faba) reared in pots are each populated with about 200 insects of the species Aphis craccivora. The treated plants are sprayed 24 hours later to drip point with an aqueous formulation containing 100 ppm of the test compound.

Two plants are used for the test compound at its given concentration and a mortality count is made after a further 24 hours. The compound of formula I effects 90–100% kill in this test.

EXAMPLE 4

Insecticidal contact action against Myzus persicae

Pea plantlets which have been reared in water to a height of 4 cm are each populated with about 200 aphids of the species Myzus persicae before the start of the test. The treated plants are then sprayed to drip point 24 hours later with an aqueous suspension containing the test compound in a concentration of 400 ppm. A mortality count is made 48 hours after application. The test is carried out at 20°–22° C. and 6% relative humidity. The compound of formula I effects 90–100% kill in this test.

EXAMPLE 5

Insecticidal systemic action against Myzus persicae (soil test)

Cabbage plants which have grown roots are transplanted in the 4- to 5-leaf stage into pots containing 60 ccm of soil. Then 50 ml of an aqueous formulation (prepared from a 25% wettable powder) of the test compound, in a concentration of 12.5 ppm, are poured direct onto the soil, without wetting the plants themselves. After 24 hours the growing parts of the plants are populated with aphids of the species Myzus persicae and plastic cylinders are then slipped over the plants to protect the aphids from any possible contact with the test substance either direct or via the gas phase. A mortality count is made 7 days after the start of the test. Two plants, each in a separate pot, are used for the test substance at its given concentration. The test is carried out at about 25° C. and 60% relative humidity.

The compound of formula I effects 90–100% kill in this test.

EXAMPLE 6

Insecticidal systemic action against Aphis craccivora and Myzus persicae

Pea plantlets which have been infested with the aphids 24 hours before the start of the test are put into 20 ml of an aqueous mixture containing 3 and 0.75 ppm respectively of the test compounds. The aqueous formulation is prepared from an emulsifiable concentrate or a wettable powder formulation of the respective test compound and is in a beaker that is sealed with a plastic lid in which holes have been punched. The root of each infested plant is pushed through a hole in the lid into the mixture. The hole is then plugged with cotton wool to hold the plant fast and to protect it from contact with the gas phase of the mixture.

The test is carried out at 20° C. and 60% relative humidity. After 2 days a count is made of aphids which are no longer able to suck (comparison with untreated controls) in order to determine whether the test cmpound absorbed by the root is able to kill the aphids on the growing upper parts of the plants.

The test results obtained in this Example are set forth in Table I below:

TABLE I

| | Systemic action - Mortality (%) | | | | | |
| --- | --- | --- | --- | --- | --- | --- |
| | Aphis craccivora | | Myzus persicae (non-resistant) | | Myzus persicae (resistant to OP compounds and carbamates) | |
| | Concentration of test compound | | | | | |
| Test compound | 3 ppm | 0.75 ppm | 3 ppm | 0.75 ppm | 3 ppm | 0.75 ppm |
| compound of formula I of this invention 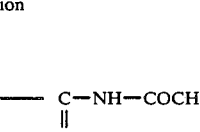 | 100% | 100% | 100% | 95% | 100% | 100% |
| compound of EP patent application 0110829 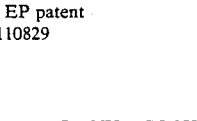 | 100% | 0% | 95% | 0% | 90% | 0% |

EXAMPLE 7

Insecticidal leaf penetration action against Aphis craccivora

A small shoot of Vicia faba, which is highly infested with aphids of the species Aphis craccivora, is placed in each of a number of 8 cm high plastic beakers (diameter about 6 cm). Each beaker is covered with a plastic lid having a punched opening of 2 cm diameter in the center. A leaf of a Vicia faba plant is then placed over the opening in the lid without separating this leaf from the potted plant. The leaf is then fixed on the beaker with a second punched lid above the opening of the first lid. From underneath, i.e. through the opening of the first lid, the aphids in the beaker then infest the leaf of the plant used as bait. An aqueous formulation of the test compound is then applied in a concentration of 100 ppm uniformly with a brush to the top side of the leaf. An inspection is then made to determine whether the test substance applied to the top side of the leaf of the plant used as bait has diffused in sufficient amount through the leaf to its underside to kill aphids sucking thereon.

The test is carried out at about 20° C. and 60% relative humidity. The evaluation of percentage mortality is made 48 hours after application of the test compound.

The compounds of formula I effects 90–100% kill in this test.

What is claimed is:

1. The compound of formula

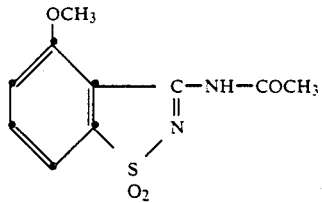

or the tautomer thereof.

2. A pesticidal composition which contains as active component an insecticidally effective amount of the compound according to claim 1, together with an insecticidally suitable carrier or other adjuvant.

3. A method of controlling insects, which comprises contacting or treating said insects and their various development stages, or the locus thereof, with an insecticidally effective amount of the compound according to claim 1.

4. A method according to claim 3, wherein the insects to be controlled are plant-destructive insects.

5. A method according to claim 4, wherein the insects to be controlled are plant-destructive sucking insects.

6. A method according to claim 5, wherein the insects to be controlled are insects of the family Aphididae.

* * * * *